(12) United States Patent
Kays et al.

(10) Patent No.: US 11,864,943 B2
(45) Date of Patent: Jan. 9, 2024

(54) METAL INJECTION MOLDING FOR STETHOSCOPE CHESTPIECE

(71) Applicant: 3M INNOVATIVE PROPERTIES COMPANY, St. Paul, MN (US)

(72) Inventors: Martin B. Kays, Columbia, MO (US); Paul R. Cassimus, Columbia, MO (US); Brandon J. Storhaug, Hugo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 460 days.

(21) Appl. No.: 17/250,943

(22) PCT Filed: Oct. 2, 2019

(86) PCT No.: PCT/US2019/054167
§ 371 (c)(1),
(2) Date: Mar. 31, 2021

(87) PCT Pub. No.: WO2020/072561
PCT Pub. Date: Apr. 9, 2020

(65) Prior Publication Data
US 2021/0369233 A1    Dec. 2, 2021

Related U.S. Application Data

(60) Provisional application No. 62/741,897, filed on Oct. 5, 2018.

(51) Int. Cl.
*A61B 7/02* (2006.01)
*B22F 3/10* (2006.01)
(Continued)

(52) U.S. Cl.
CPC ............... *A61B 7/02* (2013.01); *B22F 3/1021* (2013.01); *B22F 3/225* (2013.01); *B22F 3/227* (2013.01);
(Continued)

(58) Field of Classification Search
CPC .......... A61B 7/02; B22F 3/1021; B22F 3/225; B22F 3/227; B22F 3/24; B22F 5/10;
(Continued)

(56) References Cited

U.S. PATENT DOCUMENTS 2,543,536 A * 2/1951 Sherman ................. C08K 3/08
106/170.58
2,893,507 A    7/1959 Friedman
(Continued)

FOREIGN PATENT DOCUMENTS

CN    102670239    9/2012
CN    202568303    12/2012
(Continued)

OTHER PUBLICATIONS

European Application 19869357 Supplementary European Search Report dated May 17, 2022, 2 pages.
(Continued)

*Primary Examiner* — Forrest M Phillips

(57) ABSTRACT

The invention relates to a stethoscope comprising a stethoscope chestpiece comprising a body member having a bottom surface and an ejector mark disposed on the bottom surface. The stethoscope chestpiece has a weight of at least 50 g, a surface roughness (Ra) no greater than 1.6 microns in an unpolished state, and reflectivity (% R) of at least 60% in an unpolished state. The stethoscope chestpiece can be produced by injection molding, extruding, or pressing a metallic thermoplastic composition into a mould forming a green molded body, debinding a portion of binder material (Continued)

from green molded body forming a brown molded body without reducing the temperature by more than 80° C., and sintering the brown molded body to form the stethoscope chestpiece.

20 Claims, 7 Drawing Sheets

(51) Int. Cl.
  *B22F 3/22* (2006.01)
  *B22F 3/24* (2006.01)
  *B22F 5/10* (2006.01)
  *G10K 13/00* (2006.01)
(52) U.S. Cl.
  CPC .............. *B22F 3/24* (2013.01); *B22F 5/10* (2013.01); *G10K 13/00* (2013.01); *B22F 2003/242* (2013.01); *B22F 2003/247* (2013.01); *B22F 2998/10* (2013.01)
(58) Field of Classification Search
  CPC .......... B22F 2203/242; B22F 2203/247; B22F 2998/10; G10K 13/00
  See application file for complete search history.

(56) References Cited

U.S. PATENT DOCUMENTS

| 4,440,258 | A | 4/1984 | Packard |
| 5,420,382 | A | 5/1995 | Katz |
| 6,228,508 | B1 | 5/2001 | Kassanits |
| 6,725,966 | B2 | 4/2004 | Drummond |
| 7,682,704 | B2 | 3/2010 | Dwivedi |
| 8,016,586 | B2 | 9/2011 | Entezarian |
| 8,862,229 | B2 | 10/2014 | Stahmann |
| 9,420,987 | B2 | 8/2016 | Shan |
| 9,556,072 | B2 | 1/2017 | Ter Maat |
| 2003/0047376 | A1* | 3/2003 | Oster ................ A61B 7/02 181/131 |
| 2003/0201138 | A1* | 10/2003 | Drummond ........... A61B 7/02 181/131 |
| 2006/0018487 | A1 | 1/2006 | Smith |
| 2015/0164465 | A1* | 6/2015 | Shan ................ A61B 7/02 181/131 |
| 2016/0295705 | A1 | 10/2016 | Stoeppelmann |
| 2018/0008227 | A1 | 1/2018 | Keller |

FOREIGN PATENT DOCUMENTS

| CN | 203619584 | 6/2014 | |
| DE | 9307721 | 7/1993 | |
| EP | 0429311 A2 | 5/1991 | |
| EP | 3878579 A1 * | 9/2021 | .............. B22F 10/62 |
| WO | WO-2010009735 A2 * | 1/2010 | ......... A61K 39/0011 |
| WO | WO 2016-022380 | 2/2016 | |
| WO | WO 2017-151901 | 9/2017 | |
| WO | WO-2020152518 A1 * | 7/2020 | ............... A61B 7/02 |

OTHER PUBLICATIONS

International Search report for PCT International Application No. PCT/US2019/054167 dated Nov. 29, 2019, 4 pages.

* cited by examiner

METAL INJECTION MOLDING FOR STETHOSCOPE CHESTPIECE

CROSS REFERENCE TO RELATED APPLICATIONS

This application is a national stage filing under 35 U.S.C. 371 of PCT/US2019/054167, filed Oct. 2, 2019, which claims the benefit of Provisional Application No. 62/741,897, filed Oct. 5, 2018, the disclosures of which are incorporated by reference in their entirety herein.

BACKGROUND

Stethoscopes having non-symmetrical shapes are generally produced using an investment casting process. The investment casting process can generally involve molding a wax piece, forming a wax tree, dipping the wax tree into a sand slurry, melting the wax to form a shell, pouring the liquid metal, breaking off the shell, cutting off the tree, tumbling, cutting off a gate, grinding, followed by heat treatment. This process can cause defects such as pits and voids.

Advances into metal injection molding (MIM) or powder injection molding (PIM) have resulted in forming small intricate parts generally less than 10 g. The MIM process utilizes a powdered metal mixed with a polymeric binder to create a feedstock that is used in standard injection molding machines to generate a "green" part that is roughly 15% oversized from final part dimensions. This part then goes through a debinding process to remove the polymeric binder that leaves the part with a porous powder structure that yields a very brittle "brown" part. This part is then sintered at extremely high temperature that solidifies the metal structure, shrinking the part, and resulting in mechanical properties very similar to their wrought counterparts.

SUMMARY

In the case of injection molding, on the other hand, virtually any desired shape can be produced. However, metal powder injection molding has the disadvantages that anisotropies sometimes occur in the casting mould in the case of relatively large workpieces (e.g., greater than 50 g) and that a separate step for removing the binder has to be carried out. When applied to larger workpieces (50 g), MIM techniques can cause cracking or discoloration. This is particularly true with stethoscopes because a stethoscope chestpiece has thick and thin sections, which present issues during debinding as the difference in heating and cooling rates can generate stresses in the material causing cracks. This makes MIM ill-suited to applications where aesthetics (such as smooth mirrored surfaces) are desirable.

Aspects of the present disclosure relate to a stethoscope comprising a stethoscope chestpiece comprising a body member having a bottom surface. The stethoscope chestpiece comprises an ejector mark disposed on the bottom surface. The stethoscope chestpiece has a weight of at least 50 g, a surface roughness ($R_a$) no greater than 1.6 microns in an unpolished state, and reflectivity (% R) of at least 60% in an unpolished state. The stethoscope chestpiece can be produced by injection molding, extruding, or pressing a metallic thermoplastic composition into a mould forming a green molded body. The stethoscope chestpiece can also be produced by debinding a portion of binder material from green molded body at a temperature in the range of 100 to 200° C. over a period from 4 to 12 hours in a nitrogen-comprising atmosphere forming a brown molded body without reducing the temperature significantly. The stethoscope chestpiece can also be produced by sintering the brown molded body at a temperature in the range from 1100 to 1500° C. over a period of from 6 to 10 hours in a hydrogen or argon atmosphere to form the stethoscope chestpiece.

Aspects of the present disclosure also relate to a method of manufacturing.

DETAILED DESCRIPTION

Aspects of the present disclosure relate to a method of using metal injection molding to manufacture a stethoscope chestpiece. The stethoscope chestpiece has shown improve crack resistance by using process control conditions, feedstock selection, and ejector marks on the stethoscope chestpiece. The stethoscope chestpiece can exhibit properties that distinguish the stethoscope from traditional investment casting techniques as described herein.

As used in the instant specification and claims, "acoustical stiffness" of the diaphragm designates the mechanical stiffness of the diaphragm as influenced by the mechanical stiffness of the diaphragm material itself, the thickness of the diaphragm, the shape of the diaphragm, the diameter of the diaphragm, and the manner in which the diaphragm is attached to the stethoscope chestpiece. The phrase "plane of the diaphragm" refers to the generally planar surface of the diaphragm.

While various stethoscope chestpieces can be manufactured using metal injection molding/powder injection molding, non-symmetrical shapes are preferred. A symmetrical shape can be symmetric on a plurality of axes rotated about top-bottom axis. A non-symmetrical shape can be symmetric about only one axis (e.g., the axis intersecting a stem fitting, axis formed along the line 3-3 in FIG. 2 but not symmetrical along line 5-5. Non-symmetrical shapes generally cannot be lathed. Examples of non-symmetric shares of stethoscope chestpiece include the Master Cardiology, Master Classic, and the Classic SE by 3M (Saint Paul, Minn.). In at least one embodiment, the stethoscope chestpiece is single-sided meaning that only one diaphragm can be positioned on the stethoscope chestpiece.

Figure 1:
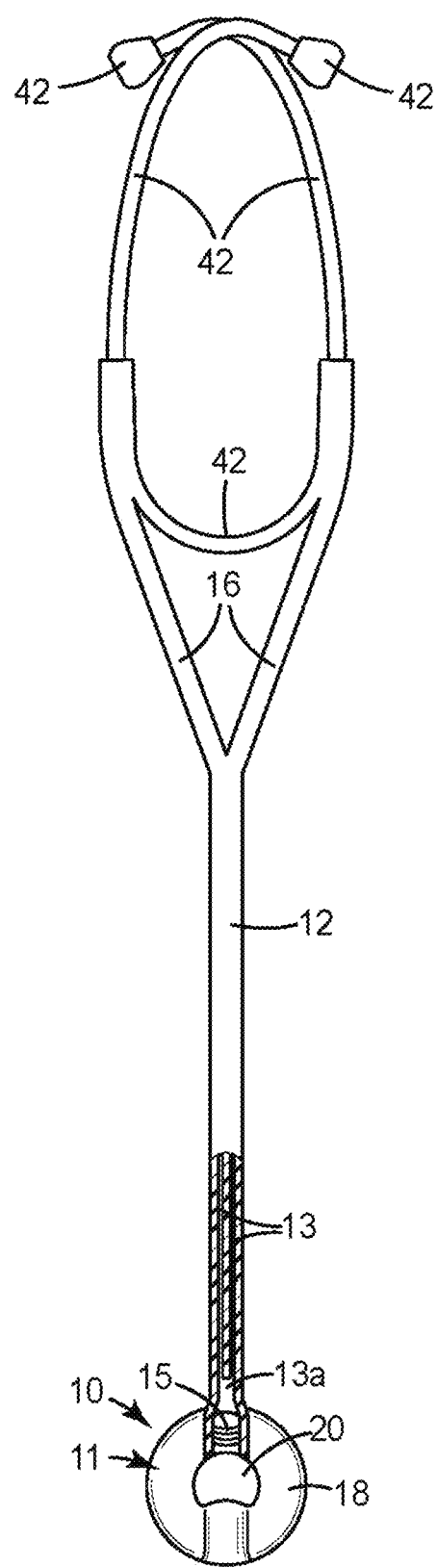
FIG. 1 is an elevational view of a stethoscope comprising an embodiment of a stethoscope chestpiece according to aspects of the present disclosure, parts thereof broken away and shown in section.

In at least one embodiment, a stethoscope from U.S. Pat. No. 4,440,258, which is incorporated by reference in its entirety can be used. For example, in FIG. 1, stethoscope chestpiece 10 comprises body member 11 formed of metallic thermoplastic compositions. Stethoscope chestpiece 10 is attached to a conventional headset such as those commercially available under the trade designation Littman by 3M (St. Paul, Minn.) which comprises elongated flexible tubing 12 which contains dual air passages 13 which run side-by-side for a major portion of the distance between stethoscope chestpiece 10 and ear tubes 14. In the lower end of flexible tubing 12 which attaches to stethoscope chestpiece 10, passages 13 merge into a single passage 13a adapted to be coupled to stem fitting 15 of stethoscope chestpiece 10. The upper end of flexible tubing 12 bifurcates into coupling arms 16, each of which attaches to one of the ear tubes 14 and each of which contains one of the ear tips 42. Ear tubes 14 are secured together by tubing 17.

Figure 2:
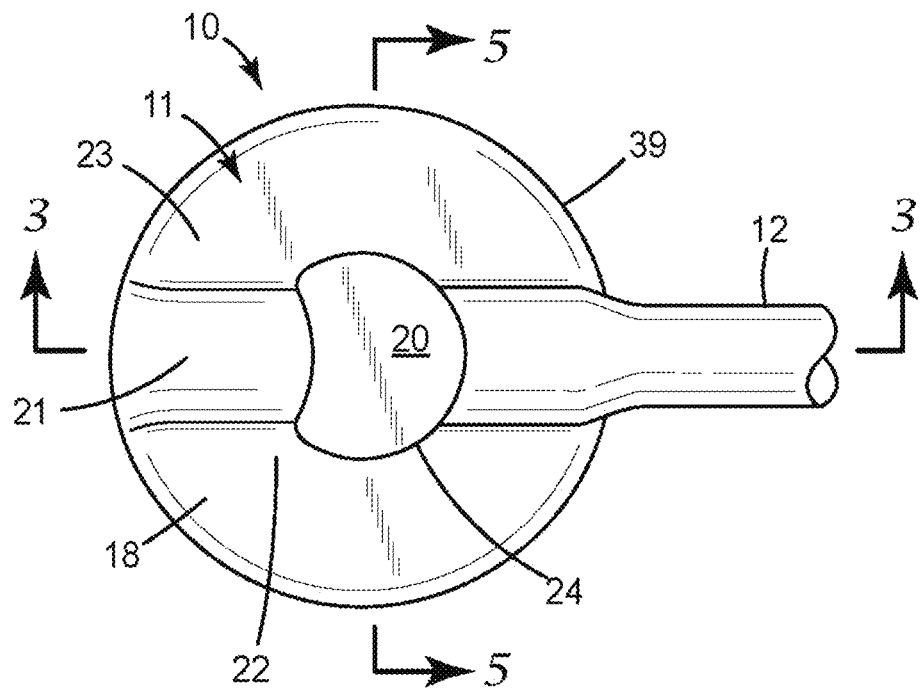
FIG. 2 is an enlarged plan view of the embodiment of the stethoscope chestpiece illustrated in FIG. 1.

The body member 11 comprises a substantially disk-like portion 18 and column 19 emanating therefrom as shown in FIG. 2. Top 20 of column 19 is substantially flat. Front section 21 of column 19 is sloped away from top 20, is concave in configuration and is curved to meet the top surface of disk-like portion 18. Side sections 22 and 23 and back section 24 are arcuate in configuration. The shape of body member 11 permits a clinician to grasp it in one of two particularly convenient ways. The clinician may grasp column 19 from the top with the index finger being placed on front section 21 and each of the thumb and the middle finger being placed on opposite sides of column 19 adjacent top 20. Alternatively, the clinician may place the index finger and middle finger adjacent disk 18 on opposite sides of column 19 (with fitting 15 passing between those fingers).

Figure 3:
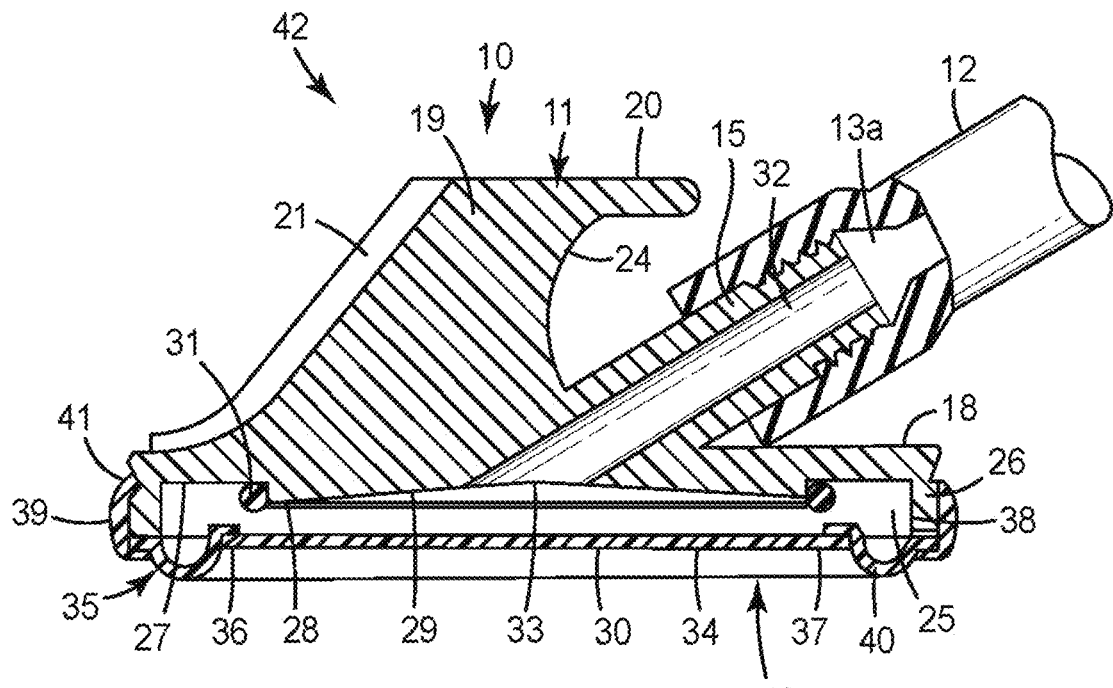
FIG. 3 is a cross sectional view taken along the line 3-3 of FIG. 2.

In FIG. 3, it is seen that body member 11 has a first generally bell-shaped recess 25, the recess 25 being defined by side wall 26, outer rim portion 27, and inner central portion or plate-like member 28 (which can be the immobilizing means). Second conical-shaped recess 29 is defined by inner central portion or plate-like member 28 which is integral with body member 11 and has a centrally sloping depression in its surface and optional O-ring 31 which is situated circumjacent plate-like member 28 and retained thereon. In at least one embodiment, the circumjacent plate-like member 28 itself can be raised further from a plane formed by the major surface of the portion adjacent to the outer rim portion 27 (the major surface contacting the compliant ring 35), thus negating the need of the O-ring 31. Body member 11 also comprises bore 32 extending from fitting 15 through body member 11 to aperture 33 within bell-shaped first recess 25 and conical-shaped second recess 29.

In at least one embodiment, the body member 11 can have an outside surface or top surface 42 at least partially defined as a region that a clinician can touch. The outside surface 42 includes the column 19. The outside surface 42 is generally polished since this surface is seen by the clinician. In at least one embodiment, the body member 11 has an inner surface or bottom surface 43. The bottom surface 43 includes a major surface of both the recess 25 and the conical-shaped second recess 29. Generally, the bottom surface 43 is overlaid by the diaphragm 34 and is not polished or seen by the clinician. The bottom surface 43 can be planar and forms a plane defined by at least one circumference.

In at least one embodiment, diaphragm 34 overlays the entirety of second conical-shaped recess 29 (and inner central portion or plate-like member 28) and at least a portion of first bell-shaped recess 25 to permit contact of diaphragm 34 with O-ring 31. Diaphragm 34 may comprise any material which is known in the art as being suitable for use as a diaphragm. Examples of suitable materials include plastics such as polyester, fiberglass-reinforced plastics, and polystyrene and metals such as stainless steel. A suitable thickness for diaphragm 34 is about 5 to 20 mils (0.013 to 0.051 centimeters). The preferred thickness for diaphragm 34 is about 10 to 12 mils (0.025 to 0.030 centimeters). A preferred diaphragm comprises a 10 mil-thick (0.025 centimeter-thick) epoxy resin-fiberglass laminate.

Optionally surrounding diaphragm 34 is suspension member or compliant ring 35 which suspends diaphragm 34 across the first bell-shaped recess 25 and allows diaphragm 34 to move in a direction generally perpendicular to the plane of the diaphragm. Compliant ring 35 is generally horseshoe-shaped in cross-section having an inner edge 37 and an outer edge 38 on either side of curved portion 40. Compliant ring 35 is attached to peripheral edge portion 36 of diaphragm 34 at inner edge 37. Outer edge 38 is attached to first bell-shaped recess 25 by means of a retaining ring or plastic fitting 39 which engages notch 41 of body member 11. In at least one embodiment, the notch 41 can have an edge having a square-like profile with non-rounded corners as a result of the finer resolution of MIM.

Preferably, the diaphragm 34 is constructed as a single piece, meaning that the diaphragm 34 is connected to the compliant ring 35 as described in U.S. Pub. No. US2018-0008227A1.

The response of stethoscope chestpiece 10 to low frequency and high frequency sounds is affected by several parameters. The thickness of diaphragm 34 affects the response and suitable thicknesses for diaphragm 34 have been discussed hereinabove. Also, the relative dimensions of first bell-shaped recess 25 and second conical-shaped recess 29 affect the response. The following have been found to be suitable dimensions for first bell-shaped recess 25 and second conical-shaped recess 29. First bell-shaped recess 25 has a diameter (as defined by side wall 26) of 2 inches (5.10 centimeters) and has a volume (as defined by diaphragm 34 and compliant ring 35 when no pressure is exerted on the exterior surface of diaphragm 34) of approximately 0.325 $in^3$ (5.33 $cm^3$). Second conical-shaped recess 29 has a diameter (as defined by O-ring 31) of 1.5 inches (3.8 centimeters) and a volume (as defined by diaphragm 34 when it is in contact with O-ring 31) of approximately 0.059 $in^3$ (0.97 $cm^3$). The distance that diaphragm 34 travels from its equilibrium position to its position in which it is in contact with O-ring 31 is approximately 0.070 inches (0.18 centimeters). As indicated above, diaphragm 34 is of a diameter which is greater than the diameter of second conical-shaped recess 29 in this embodiment. A diaphragm having a 1.75 inch (4.45-centimeter) diameter has been found to be suitable in a stethoscope chestpiece comprising first bell-shaped recess 25 and second conical-shaped recess 29 of the above indicated dimensions. A compliant ring 35 which includes curved portion 40 having a radius of curvature of 0.047 inches (0.12 centimeters) has been found to provide the desired freedom of movement of diaphragm 34.

Figure 4:
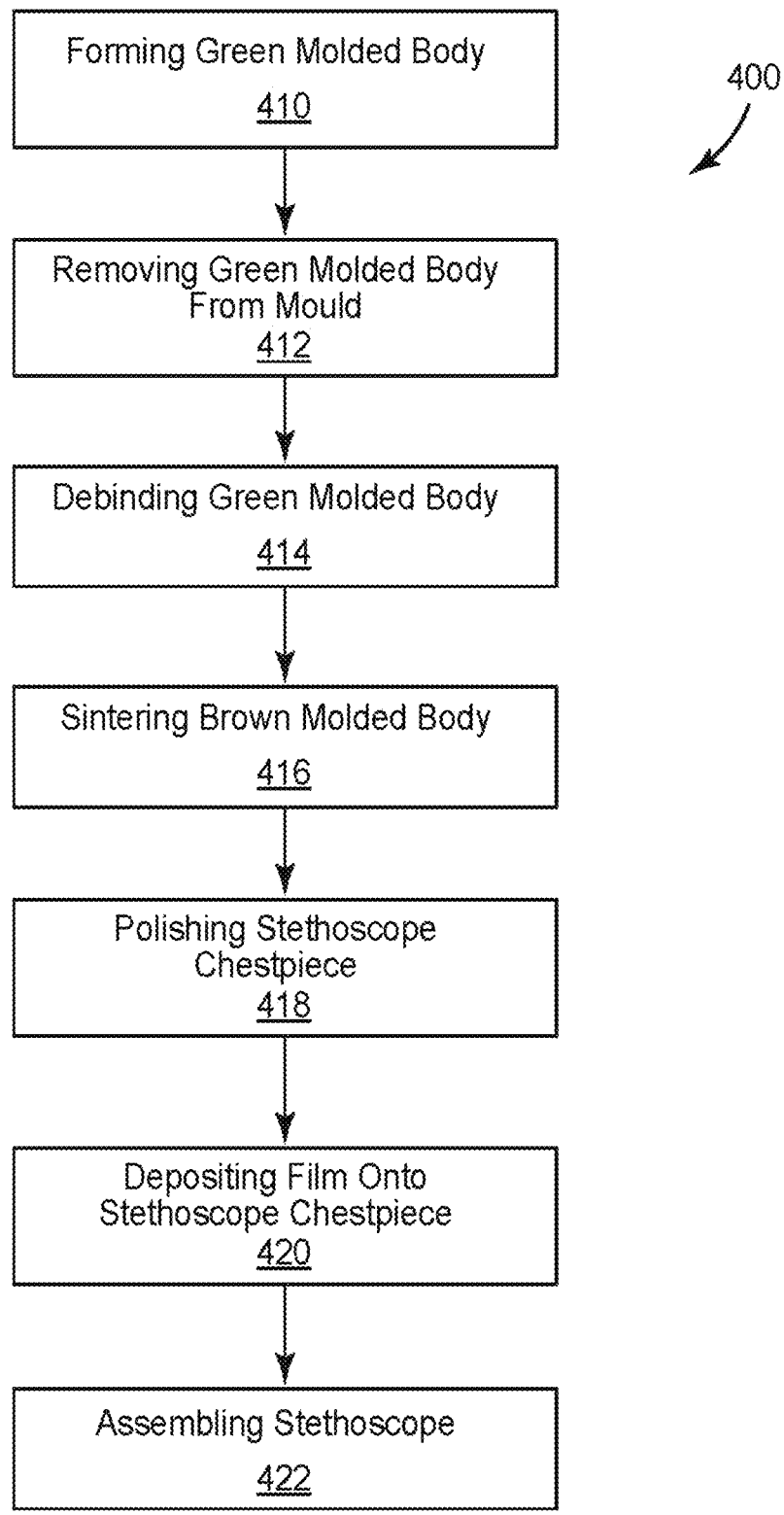
FIG. 4 is a flowchart of a method of making a stethoscope.

FIG. 4 illustrates a flowchart of a method 400 of making a stethoscope. The method 400 includes making a chestpiece, e.g., blocks 410 through 420, and assembling the stethoscope, e.g., block 422.

The method 400 can begin at block 410 where a green molded body is formed. The green molded body can be metallic thermoplastic and can be obtained by injection molding, extruding, or pressing of metallic thermoplastic compositions or thermoplastic molding compositions comprising metal powders. Examples of metal powders are powders of Fe, Al, Cu, Nb, Ti, Mn, V, Ni, Cr, Co, Mo, W and Si, and combinations thereof. Stethoscope chestpieces which are preferred for the purposes of the present invention are those which can be obtained from powder injection molding compositions, particularly preferably from powder injection molding compositions of Fe and Cr.

For the purposes of the present disclosure, the terms "injection molding" (also referred to as powder injection molding), "extrusion" and "pressing" are used in the sense of processes from powder technology, in particular powder metallurgy, in which, for example, a shaped body from which the binder is subsequently removed and which is then sintered to produce the finished workpiece is produced by injection molding of a thermoplastic injection molding composition comprising metal or ceramic powder and a proportion of usually at least 30% by volume of a thermoplastic binder. Thus, the mould for metal injection molding is generally larger than the finished stethoscope chestpiece.

In at least one embodiment, the injection molding of the metallic thermoplastic composition can occur at an elevated temperature sufficient to bind portions of the metallic thermoplastic compositions inside of the mould. The mould is a hollow container used to give shape a molten metallic thermoplastic material, when the material cools and hardens. The mould is a negative impression of the intended stethoscope chestpiece. The mould as defined herein can be a negative of the stethoscope chestpiece described herein.

The metallic thermoplastic composition can include both a binder. The polyoxymethalene homopolymers and copolymers mentioned as binders and their preparation are known to those skilled in the art and are described in the literature. The homopolymers are usually prepared by polymerization (mostly catalyzed polymerization) of formaldehyde or trioxane. To prepare polyoxymethylene copolymers, a cyclic ether or a plurality of cyclic ethers is/are usually used as comonomer together with formaldehyde and/or trioxane in the polymerization, so that the polyoxymethylene chain with its sequence of ($—OCH_2$)-units is interrupted by units in which more than one carbon atom is present between two oxygen atoms. Examples of cyclic ethers which are suitable as comonomers are ethylene oxide, 1,2-propylene oxide, 1,2-butylene oxide, 1,3-dioxane, 1,3-dioxolane, dioxepane, linear oligoformals and polyformals such as polydioxolane or polydioxepane and also oxymethylene terpolymers.

In general, the binder comprises at least 80% by weight of polyoxymethylene (POM) and can additionally comprise further polymers, for example polystyrene, polypropylene, polyethylene and ethylene-vinyl acetate copolymers and also further auxiliaries which may be necessary, e.g. dispersants, plasticizers and mold release agents. In particular, the further polymers mentioned, e.g. polystyrene, polypropylene, polyethylene and ethylene-vinyl acetate copolymers, and also any further auxiliaries which may be necessary, e.g. dispersants, plasticizers and mold release agents, are removed from the shaped part.

In at least one embodiment, the metallic thermoplastic composition is commercially available under the trade designation Catamold, model: LG plus from BASF (Florham Park, N.J.).

Once molded, then the green molded body can be optionally removed, e.g., demolded, in block 412. The green molded body can be removed in order to allow shrinkage and avoid problems during the debinding and sintering process. In at least one embodiment, the removal can include applying one or more ejectors (comprising ejector pins) to the green molded body to remove the green molded body from the mould. In at least one embodiment, it may be beneficial for the ejectors to contact the part over the largest possible area and without tilting. The ejector pins can be any shape and be positioned roughly evenly along the stethoscope chestpiece. Preferably, the ejectors pins can contact an unseen or unpolished area of the stethoscope chestpiece such as the bottom. Once the ejector pins contact the green molded body, ejector marks can be formed in the green molded body as described herein.

In at least one embodiment, the green molded body can be removed via a vacuum method which may leave a positive protruding area within the green molded body.

In block 414, a portion of binder material from the green molded body can be debound to form the brown molded body. For example, thermal debinding, or pyrolysis, can be used. The green molded body is heated in a closely controlled oven up to a temperature just below the softening point of the binder.

In at least one embodiment, a binder can undergo gaseous decomposition. For example, if the binder is polyacetal, debinding can occur at or around 110 deg. C., which is below the melting range of polyacetal, 150° C.-170° C. Thus, the polymer can be directly converted from a solid into a gas. After the polyacetal is removed, a residual amount (usually around 10 weight % of the original binder content) of an acid-resistant binder component may remain. Depending on the material used, the temperature of a debinding oven can be from 100 C to 200 C, 100 C to 140 C, preferably 110-120 C. In at least one embodiment, block 414 can occur in a nitrogen comprising atmosphere, wherein nitric acid and formaldehyde are vented.

Solvent debinding is an alternative process that improves the debinding rate verses pyrolysis. The parts are immersed in liquid or vapor of an extracting solvent. The solvent accelerates the removal of binder from the parts and helps open-up porosity in the part. Solvent debinding still requires that the residual binder and solvent must be removed from the part thermally. Possible solvents may include nitric acid.

If the binder undergoes thermal debinding, a binder removal oven or debinding oven can be used. The binder removal oven is an oven through which the shaped bodies travel in a transport direction while being brought to the above-defined temperatures for the above-defined periods of time. Various designs of debinding ovens are commercially available from manufacturers such as CMFunaces, Inc (Bloomfield, N.J.) or Elnik Systems, LLC (Cedar Grove, N.J.).

While some debinding methods involve the transport from a first debinding oven to a second debinding oven, this may introduce partial cooling which was found to be detrimental. An aspect of the present disclosure is the continuous debinding (e.g., debinding without transferring ovens or otherwise without significant drops in temperature). For example, during debinding, the temperature does not more than 80° C., more than 70° C., more than 60° C., more than 50° C., more than 40° C., more than 30° C., more than 20° C., more than 10° C., or more than 5° C. during the debinding period.

In at least one embodiment, the total debinding can occur between 4 to 12 hours, 4 to 10 hours, 4 to 8 hours, 4 to 7 hours, 4 to 6 hours, or 4 to 5 hours in a nitrogen-comprising atmosphere.

In block 416, the brown molded body can be sintered at a temperature in the range from 1100 to 1500° C. over a period of from 6 to 10 hours to produce a stethoscope chestpiece (unpolished). In at least one embodiment, the sintering may occur in a pure hydrogen or argon atmosphere to form the stethoscope chestpiece.

The sintering time, i.e. the hold time at the sintering temperature, is generally set so that the sintered shaped parts are sintered to sufficient density. Sintering is preferably carried out so that the sintering process is shorter relative to debinding. In general, the sintering process (including the heating ramp up phase but without the cooling phase) will be able to be concluded after 4 to 12 hours, 4 to 10 hours, 6 to 10 hours, 8 to 10 hours, 4 to 8 hours, 4 to 7 hours, or 4 to 6 hours for a stethoscope chestpiece. In at least one embodiment, the total time in both the sintering process and debinding process can be between 6 to 15 hours, 6 to 12 hours, 6 to 10 hours, or 6 to 8 hours.

Various sintering apparati may be used and are commercially available from manufacturers such as CMFunaces, Inc (Bloomfield, N.J.) or Elnik Systems, LLC (Cedar Grove, N.J.). After sintering, any desired after-treatment, for example sinter hardening, austenite formation, annealing, hardening, upgrading, carburization, case hardening, carbonitriding, nitriding, steam treatment, solution heat treatment, quenching in water or oil and/or hot isostatic pressing of the sintered shaped parts or a combination of these treatment steps, can be carried out. Some of these treatment steps, for instance sinter hardening, nitriding or carbonitriding can also be carried out in a known way during sintering. Once produced, the stethoscope chestpiece can be removed from the line and optionally shipped for polishing.

The unpolished stethoscope chestpiece produced by injection molding can have properties that are unexpectedly better than those produced using investment casting techniques. For example, the surface roughness of an injection molded stethoscope chestpiece is as follows:

$R_z$ can be no greater than 10.4 microns, no greater than 10 microns, no greater than 9 microns, no greater than 8 microns, no greater than 7 microns, no greater than 6 microns, no greater than 5 microns, no greater than 4 microns, no greater than 3 microns.

$R_a$ can be no greater than 1.6 microns, no greater than 1.5 microns, no greater than 1.4 microns, no greater than 1.3 microns, no greater than 1.2 microns, no greater than 1.1 microns, no greater than 1.0 microns.

$R_m$ can be no greater than 12.4 microns, no greater than 12 microns, no greater than 11 microns, no greater than 10 microns, no greater than 9 microns, no greater than 8 microns, no greater than 7 microns, no greater than 6 microns, no greater than 5 microns, no greater than 4 microns, no greater than 3 microns. The surface roughness can be measured according to ASME B46.1-2009.

Further, the unpolished injection molded stethoscope chestpiece can have better manufacturing yields, improved finish, and corrosion resistance compared to an investment cast unpolished stethoscope chestpiece. The resulting stethoscope chestpiece can have a weight of at least 50 g, at least 55 g, at least 60 g, at least 70 g, at least 75 g, at least 80 g, at least 85 g, at least 90 g, or at least 94 g which is significantly heavier than smaller metal injection molded parts.

In at least one embodiment, the reflectance can be measured according to ASTM E1331-15. The unpolished injection molded stethoscope chestpiece can have a percent reflectance (% R) of at least 60%, at least 65%, at least 70%, at least 75%, at least 80%, at least 85%, at least 90%, at least 95%, at least 96%, at least 97%, at least 98%, or at least 99% at a wavelength of 400 to 650 nm.

Figure 9:
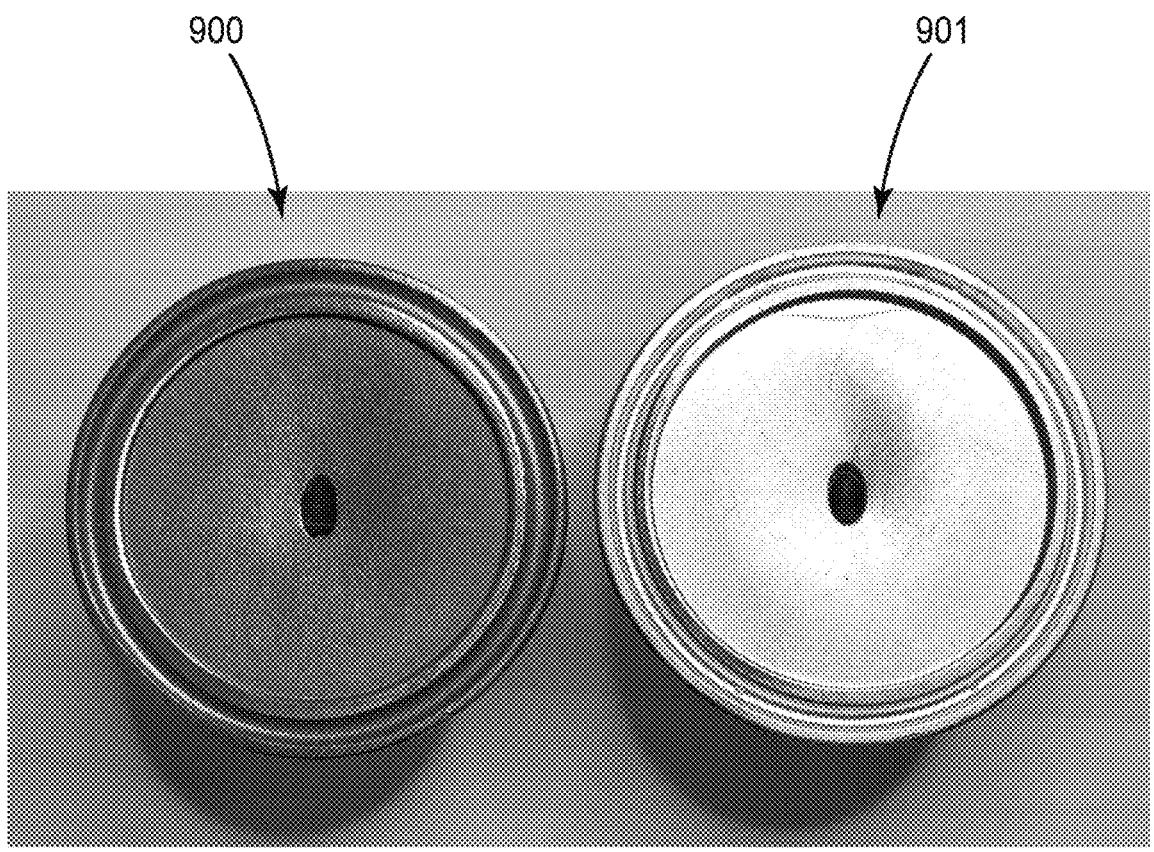
FIG. 9 is a photograph of a stethoscope chestpiece formed using investment casting and a stethoscope chestpiece formed using injection molding.
Figure 10:
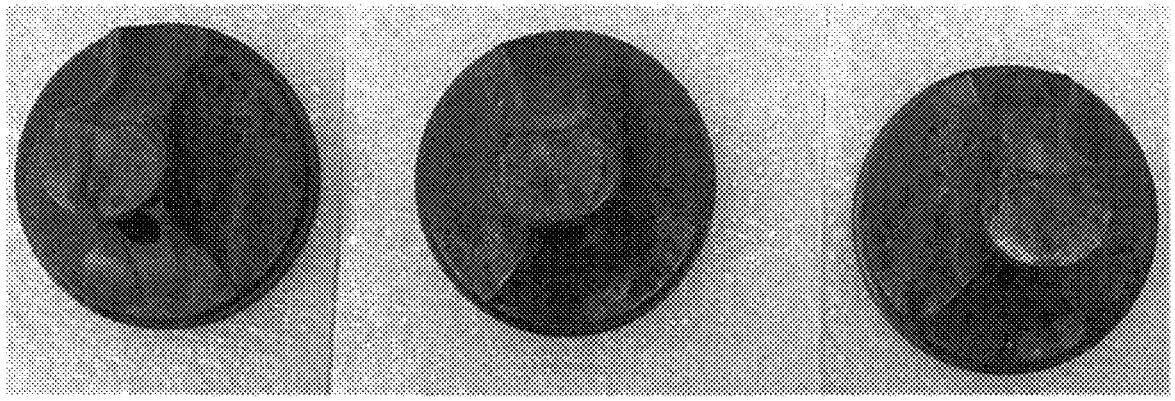
FIG. 10 is a photograph of a corroded stethoscope chestpiece formed using metal injection molding.
Figure 11:
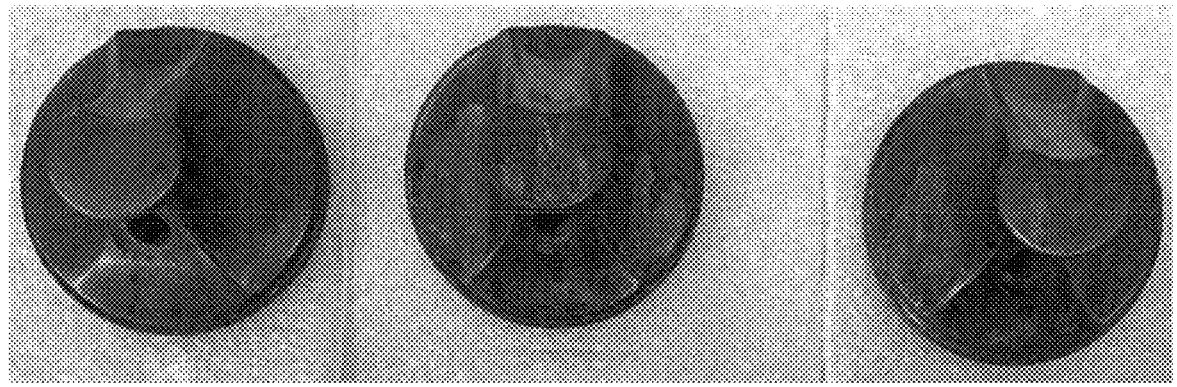
FIG. 11 is a photograph of a corroded stethoscope chestpiece formed using investment casting.
Figure 12:
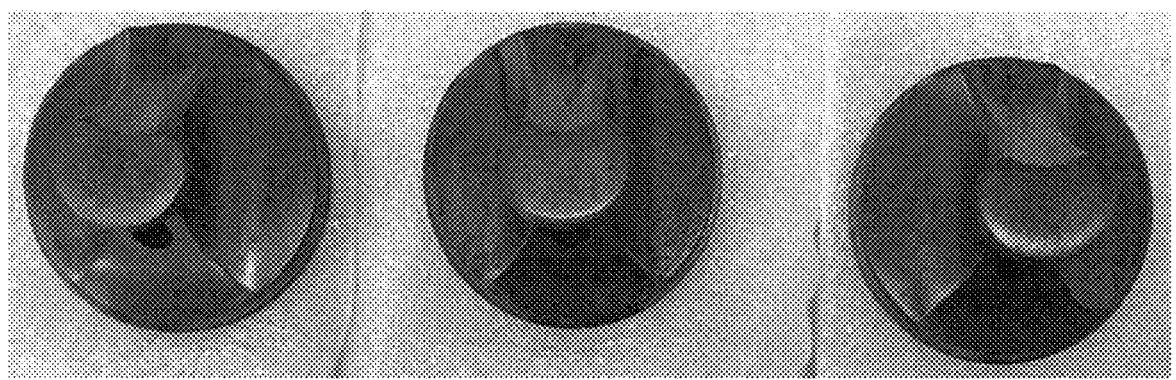
FIG. 12 is a photograph of a corroded stethoscope chestpiece formed using metal injection molding.

For example, FIG. 9 illustrates an investment cast stethoscope chestpiece 900 side-by-side with a metal injection molded stethoscope chestpiece 901. The MIM stethoscope chestpiece 901 has a silver diffusely reflective finish versus the dull gray of the investment cast stethoscope chestpiece 900.

In block 418, the stethoscope chestpiece 418 can optionally be polished to further enhance the visual appearance of the stethoscope chestpiece. Polishing may produce a mirrored finish and allows any pits or surface roughness to be smoothed out. Finish on the mirror polished parts must be nearly perfect, e.g., no pits, bumps, scratches, blemishes, or stains.

In block 420, a film can also optionally be deposited onto the stethoscope chestpiece. Various thin metallic films can be applied using physical vapor deposition, or chroming. With physical vapor deposition, a brass-colored or black-colored finish can be applied to the stethoscope chestpiece.

In block 422, the stethoscope can be assembled. The stethoscope can be assembled by attaching a stem into the stem fitting or a portion of the stethoscope chestpiece, attaching tubing to the stem. The tubing wherein the tubing is also connected to a yoke (e.g., the coupling arms 16 in FIG. 1), eartubes, and eartips. The assembly can also include attaching a diaphragm to the stethoscope chestpiece. Once assembled, the stethoscope can be packaged in an appropriate packaging.

Figure 5:
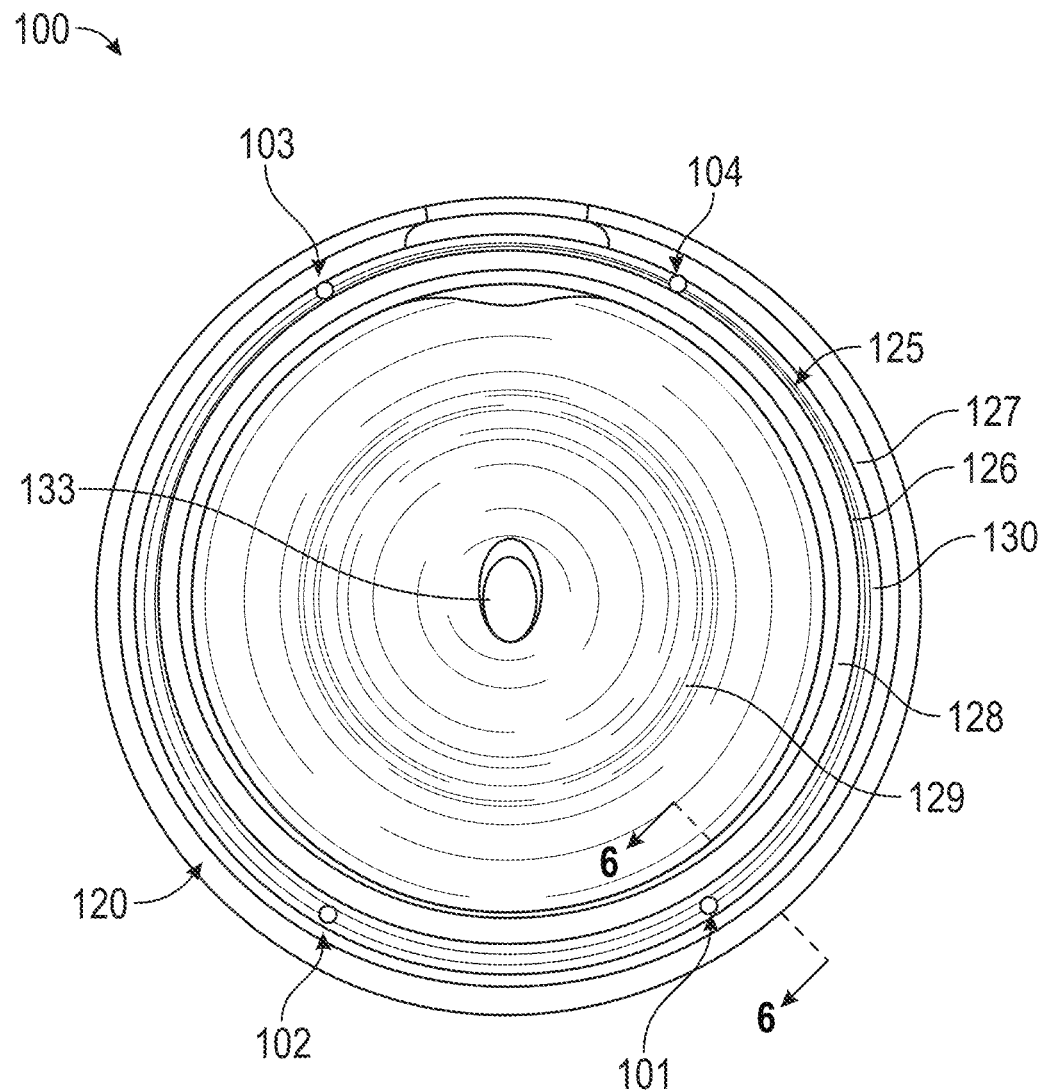
FIG. 5 is a flowchart of a bottom view of a stethoscope chestpiece formed.

FIG. 5 illustrates a unpolished injection molded stethoscope chestpiece 100, according to various embodiments. The stethoscope chestpiece 100 comprises a plurality of ejector marks 101, 102, 103, 104. The components of stethoscope chestpiece 100 can be similar to that of stethoscope chestpiece 10 in FIGS. 1-3 with similar numbering. For example, recess 125 refers to a region between the outer edge 120 The recess 125 can be recessed relative to the plate-like member 128 and the outer edge 120. The recess 125 can be defined by at least two side walls, side wall 126 and outer rim portion 127 which is shown tapering into a nadir 130. In at least one embodiment, the nadir 130 may be a planar bottom surface.

The ejector marks 101-104 can be marks from ejector pins or vacuums used in the demolding process. In at least one embodiment, the ejector marks 101-104 are equally spaced along the perimeter. The ejector marks 101-104 can also be spaced to allow even removal from a mould. Although 4 ejector marks are pictured, any number of ejector marks can be present. For example, a stethoscope chestpiece can include at least one ejector mark, at least two ejector marks (i.e., a plurality of ejector marks), at least 4 ejector marks, etc. In at least one embodiment, the total number of ejector marks is an even number (e.g., 2, 4, 6).

As shown in stethoscope chestpiece 100, the ejector marks 103, 104 are positioned toward the front whereas ejector marks 101, 102 are positioned toward the back of the stethoscope chestpiece 100 (proximate to the stem cavity). Since the top of the stethoscope chestpiece forms a complex portion overhanging the stem, the ejector marks 103, 104 are closer together around the circumference of the recess 125 near the areas where force can be applied evenly to remove the top from a mould. Ejector marks 102 and 103 have a greater distance (at least 2 times) than the distance between 103 and 103 following the circumference of the recess 125.

Figure 6:
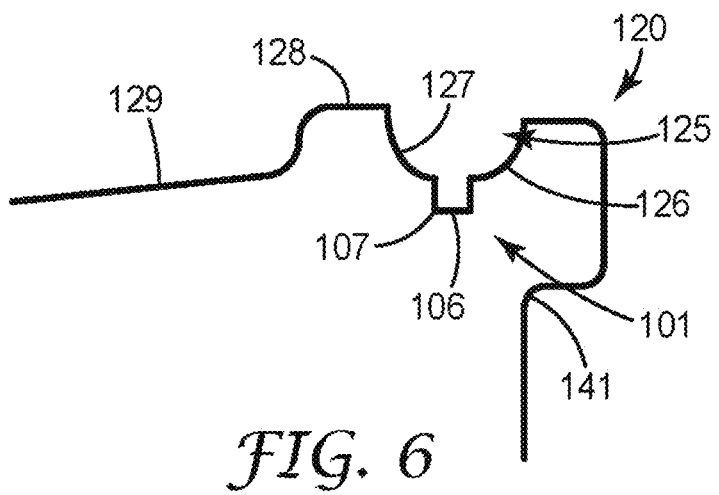
FIG. 6 is a partial cross-section view of the stethoscope chestpiece taken along the line 6-6 of FIG. 5.
Figure 7:
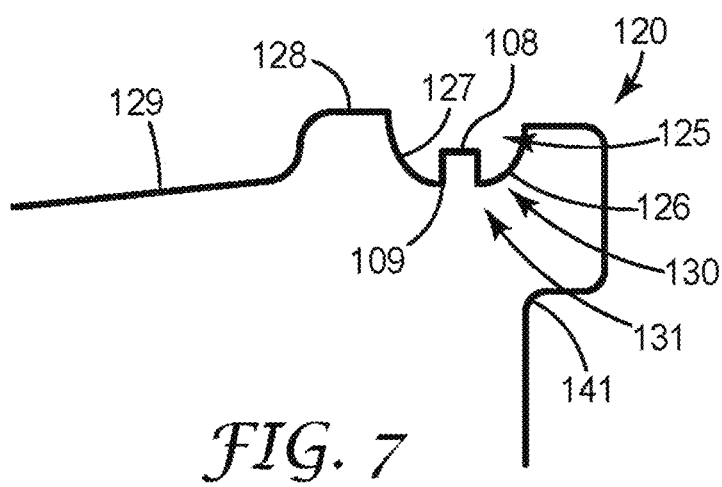
FIG. 7 is a partial cross-section taken of another embodiment of a stethoscope chestpiece similar to the view of FIG. 6.
Figure 8:
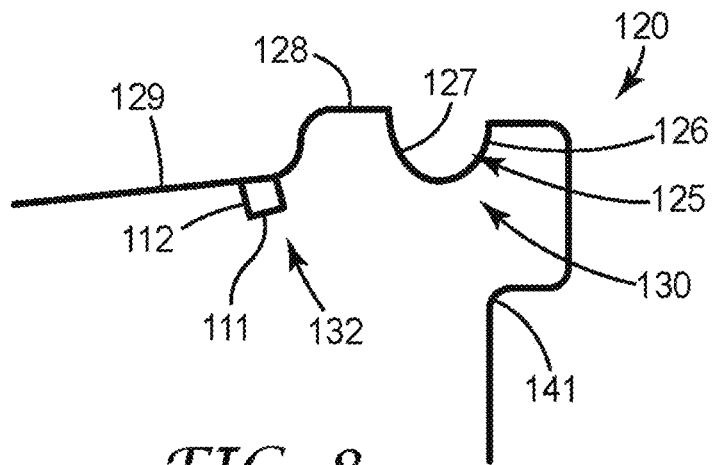
FIG. 8 is a partial cross-section taken of another embodiment of a stethoscope chestpiece similar to the view of FIG. 6.

In at least one embodiment, the ejector marks 101-104 are positioned proximate to an edge 120, e.g., in recess 125 (e.g., FIGS. 6 and 7, on plate-like member 128, or even positioned in the conical shaped second recess 129 as shown in FIG. 8. In at least one embodiment, the ejector marks can be any shape, however circular shapes can be useful in reducing corners and sharp edges. Although shown as relatively planar to the surface established by 128, the ejector marks 101-104 can be tapered depending on the mould shape.

FIG. 6 illustrates the actual cross section corresponding to FIG. 5, FIGS. 7 and 8 illustrate embodiments of potential cross-sections along a similar view. The ejector marks 101-104 can be recessed relative to a plane of a surface or protruded. FIG. 6 illustrates recessed ejector mark 101 can be recessed relative to the nadir 130. The ejector mark 101 can have a bottom surface 106 and one or more side walls 107. The ejector mark 101 can have a depth of less than 4 mm, 3 mm, 2 mm, 1 mm, 0.8 mm, 0.6 mm, 0.4 mm, or 0.2 mm. In at least one embodiment, the ejector mark 101 does not extend to a depth beyond notch 41.

In at least one embodiment, the ejector marks 101-104 have an area (measured by the bottom surface 106) of no greater than 5 mm$^2$, no greater than 4 mm$^2$, no greater than 3 mm$^2$, no greater than 2 mm$^2$, no greater than 1 mm$^2$, no greater than 0.5 mm$^2$. In at least one embodiment, the ejector marks 101-104 can have a volume no greater than no greater than 5 mm$^3$, no greater than 4 mm$^3$, no greater than 3 mm$^3$, no greater than 2 mm$^3$, no greater than 1 mm$^3$, no greater than 0.5 mm$^3$.

FIG. 7 illustrates a protruding ejector mark 131. The protruding ejector mark 131 can be formed by a vacuum assist of removing the green molded body from the mould. The ejector mark 131 can have a top surface 108 and one or more side walls 109. The protruding ejector mark 131 can have a side wall 109 height of no greater than the plate-like member 128.

FIG. 8 illustrates a recessed ejector mark 132 (having bottom surface 111 and side wall 112) that is positioned within the conical-shaped recess 129.

It is to be understood that other variations and modifications can be made without departing from the spirit and scope of the invention.

Examples

Materials:

Test Methods:

Corrosion Test

The test method used for corrosion was modified from ASTM D 1654, Standard Test Method for Evaluation of Painted or Coated Specimens Subjected to Corrosive Environments. The samples were then visually inspected for rust or corrosion and the results recorded in Table 2.

Visual Test:

Stethoscope chestpieces were inspected visually and any imperfections were noted in Table 1.

Preparation:

EX1 was prepared using a metal injection molding technique using 17-4PH F as a feedstock and molded into the same specifications as a Master Cardiology Stethoscope Chestpiece from 3M. The green molded body was sintered, continuously, for at least 4 hours at a temperature of at least 100 C in a nitrogen atmosphere. The temperature of the sintering oven did not drop more than 10 deg. C. while sintering. A mirror finish was achieved by polishing the chestpiece.

EX2 was prepared using a metal injection molding technique using 316LA as a feedstock and molded into the same specifications as a Master Cardiology Stethoscope Chestpiece from 3M. The process conditions were the same as in EX1.

EX3 was prepared using a metal injection molding technique using 316LG+ as a feedstock and molded into the same specifications as a Master Cardiology Stethoscope Chestpiece from 3M. The process conditions were the same as in EX1.

CE1 was prepared using 17-4PH as a feedstock in an investment casting method used in production of existing Master Cardiology Stethoscope Chestpieces. A mirror finish was achieved by polishing the chestpiece.

EX4 was prepared as in EX1 except that a smoke-colored coating was applied using physical vapor deposition (PVD).

EX5 was prepared as in EX2 except that a smoke-colored was applied using physical vapor deposition (PVD).

CE2 was prepared as in CE1 except that a smoke-colored was applied using physical vapor deposition (PVD).

Results

TABLE 1

| | Visual Inspection | |
|---|---|---|
| Sample | Appearance | Notes |
| EX1 | Not acceptable | Blemishes in the polish and small pits |
| EX2 | Not acceptable | Small pits and bumps across entire surface |

| Steel type | Product type and supplier (location) | Melt Flow Index (MFI) (Test Method: ISO 1133 (190 C. 21.6 kg)) | Sintered density (Test Method: ISO 3369) |
|---|---|---|---|
| 17-4PH | Stainless Steel, source unknown (Available from, for example, Specialty Steel Supply, Pinehurst, TX) | Not applicable | Not applicable |
| 17-4PH F | Catamold 17-4PH-F from BASF Corporation (Florham Park, NJ) | 517 g/10 min | 7.63 g/cm$^3$ |
| 316LA | Catamold 316LA from BASF Corporation (Florham Park, NJ) | 562 g/10 min | 7.84 g/cm$^3$ |
| 316LG+ | Catamold 316LG+ from BASF Corporation (Florham Park, NJ) | 1000 g/10 min | 7.96 g/cm$^3$ |

TABLE 1-continued

| | Visual Inspection | |
|---|---|---|
| Sample | Appearance | Notes |
| EX3 | Excellent | Minimal pits, near perfect mirror finish |
| CE1 | Acceptable | Current Production |

For EX1, it passed initial review of small lot quantities, but issues were noticed when larger production runs were inspected. During the inspection of the larger production lots, blemishes were noticed on about 30% of the parts reviewed and was considered an unacceptable yield for this process. The blemishes were seen on a variety of surfaces on the polished area of the chestpiece with varying severity. The blemishes were attributed to the material and had pitting which rules out the EX1 for the mirror polished application.

For EX2, issues were noticed right away once the initial samples were run through the mirror polishing process. Small pits and bumps were consistently seen across the entire surface of the parts. This surface imperfection caused EX2 to be unsuitable for mirror polish applications.

For EX3, these parts showed a near perfect mirror finish that satisfies the visual specification.

TABLE 2

| Corrosion Test Results | | |
|---|---|---|
| Sample | FIG. | Corrosion |
| EX4 | 10 | High |
| EX5 | 12 | Low |
| CE2 | 11 | Medium |

The results from corrosion testing can be seen in FIGS. 10-13 for the standard Smoke coating on the Examples EX4, EX5, and CE2. The EX4 samples were once again worse than the CE2 samples, while the EX5 performed significantly better than the CE2 sample.

List of Illustrative Embodiments

1. A stethoscope chestpiece comprising:
   a body member having a first generally bell-shaped recess with an inner central portion, an outer rim portion and a bore extending through the body member communicating with the inner central portion of the first recess;
   an ejector mark proximate to the outer rim portion or inner central portion;
   wherein the stethoscope chestpiece has a weight of at least 50 g, and a surface roughness ($R_a$) no greater than 1.6 microns in an unpolished state and reflectivity (% R) of at least 70% in an unpolished state.
1a. The stethoscope chestpiece of embodiment 1, wherein the stethoscope chestpiece has been produced by
   injection molding, extruding, or pressing a metallic thermoplastic composition into a mould forming a green molded body.
1a1. The stethoscope chestpiece of embodiment 1a, further comprising:
   debinding a portion of binder material from green molded body at a temperature in the range of 100 to 200° C. over a period from 4 to 12 hours in a nitrogen-comprising atmosphere forming a brown molded body without reducing the temperature;
   sintering the brown molded body at a temperature in the range from 1100 to 1500° C. over a period of from 6 to 10 hours in a hydrogen or argon atmosphere to form the stethoscope chestpiece.
1a2. The stethoscope chestpiece of embodiment 1a1, wherein the metallic thermoplastic composition has a melt flow index of at least 800 g/10 mins as measured using ISO 1133 (190 deg. C., 21.6 kg).
1a3. The stethoscope chestpiece of embodiment 1a1, wherein the stethoscope chestpiece has a sintered density of 7.9 g/cm³ as measured by ISO 3369.
1b. A stethoscope chestpiece comprising:
   a body member having a bottom surface;
   an ejector mark disposed on the bottom surface;
   wherein the stethoscope chestpiece has a weight of at least 50 g, and a surface roughness ($R_a$) no greater than 1.6 microns in an unpolished state and reflectivity (% R) of at least 70% in an unpolished state.
1c. The stethoscope chestpiece of embodiment 1b, wherein the stethoscope chestpiece has been produced by
   injection molding, extruding, or pressing a metallic thermoplastic composition into a mould forming a green molded body,
   debinding a portion of binder material from green molded body at a temperature in the range of 100 to 200° C. over a period from 4 to 12 hours in an nitrogen-comprising atmosphere forming a brown molded body without reducing the temperature;
   sintering the brown molded body at a temperature in the range from 1100 to 1500° C. over a period of from 6 to 10 hours in a hydrogen or argon atmosphere to form the stethoscope chestpiece.
2. The stethoscope chestpiece of embodiment 1-1c, wherein the metallic thermoplastic composition comprises at least one polyoxymethylene homopolymer or copolymer as a binder and steel.
3. The stethoscope chestpiece of embodiment 2, wherein the metallic thermoplastic composition comprises iron and chromium.
4. The stethoscope chestpiece of embodiment 3, wherein the metallic thermoplastic composition is Catamold LG+.
5. The stethoscope chestpiece of any of embodiments 1 to 4, wherein the stethoscope chestpiece is single-sided meaning that only one diaphragm can be positioned on the stethoscope chestpiece.
6. The stethoscope chestpiece of any of embodiments 1 to 5, wherein the stethoscope chestpiece has a weight of at least 55 g.
7. The stethoscope chestpiece of any of embodiments 1 to 6, wherein the stethoscope chestpiece has a weight of at least 85 g.
8. The stethoscope chestpiece of any of embodiments 1 to 7, wherein the stethoscope chestpiece has a weight of at least 94 g.
9. The stethoscope chestpiece of any of embodiments 1 to 8, wherein the stethoscope chestpiece is further polished to a reflective finish.
10. The stethoscope chestpiece of any of embodiments 1 to 9, wherein the stethoscope chestpiece comprises a thin metallic film deposited by physical vapor deposition.
11. The stethoscope chestpiece of any of embodiments 1 to 10, wherein an edge of the stethoscope chestpiece has a square like profile with non-rounded corners.
11a. The stethoscope chestpiece of any of embodiments 1 to 11, wherein the ejector mark is recessed.
11b. The stethoscope chestpiece of any of embodiments 1 to 11a, wherein the ejector mark is protruding.

11c. The stethoscope chestpiece of any of embodiments 1 to 11b, wherein the ejector mark is caused by the contact of an ejector pin with the green molded body.

11d. The stethoscope chestpiece of any of embodiments 1 to 11c, wherein the ejector mark comprises a side wall and at least one major surface contacting the side wall.

11e. The stethoscope chestpiece of any of embodiments 1 to 11d, wherein the stethoscope chestpiece is non-symmetrical.

11f. The stethoscope chestpiece of any of embodiments 1 to 11e, wherein the stethoscope chestpiece has a thick portion and a thin portion.

12. The stethoscope chestpiece of any of embodiments 1 to 11, further comprising:

a body member having a first generally bell-shaped recess with an inner central portion, an outer rim portion and a bore extending through the body member communicating with the central portion of the first recess;

immobilizing means situated on the body member and located within the first recess at about the central portion, the immobilizing means adapted to be contacted by a diaphragm when the diaphragm is in the inner position so that the stethoscope chestpiece will pass low frequency sounds and attenuate high frequency sounds when the diaphragm is in the outer position and between the outer and inner positions, and when the diaphragm is in the inner position the acoustical stiffness of the diaphragm will be sufficiently higher than the first acoustical stiffness so that the stethoscope chestpiece will pass high frequency sounds and attenuate low frequency sounds.

13. The stethoscope chestpiece of embodiment 12, further comprising a second conical-shaped recess located within the first bell-shaped recess and emanating from the base of the first bell-shaped recess, the second recess being formed by the immobilizing means and the central portion of the body member.

14. The stethoscope chestpiece of embodiment 12, wherein the suspension member is a cylindrical-shaped foam member.

15. The stethoscope chestpiece of embodiment 12, wherein the suspension member is a compression spring.

16. The stethoscope chestpiece of any of embodiments 12 to 15, wherein the ejector mark is disposed within the first generally bell-shaped recess.

17. The stethoscope chestpiece of any of embodiments 1 to 11, comprising:

a body member having a first generally bell-shaped recess with an inner central portion, an outer rim portion, and a bore extending through the body member communicating with the central portion of the first recess;

immobilizing means situated on the body member and located within the first recess at about the boundary between the outer rim portion and the inner central portion and together with the central portion forming second shallow and generally conical-shaped recess within the first recess, the immobilizing means adapted to be contacted by a diaphragm and to immobilize the diaphragm when the diaphragm is in the inner position so that the stethoscope chestpiece will pass low frequency sounds and attenuate high frequency sounds when the diaphragm is in the outer position and between the outer and inner positions, and when the diaphragm is in the inner position the acoustical stiffness of the diaphragm will be significantly higher than the first acoustical stiffness so that the stethoscope chestpiece will pass high frequency sounds and attenuate low frequency sounds.

18. The stethoscope chestpiece of embodiment 17, wherein the second conical-shaped recess is formed by a plate-like member having a gradually sloping central depression therein 18a. The stethoscope chestpiece of embodiment 18, further comprising: a resilient O-ring circumjacent the plate-like member, the O-ring having a thickness which is greater in dimension than the maximum thickness of the plate-like member at its periphery and constituting the immobilizing means.

19 A stethoscope chestpiece of embodiment 17, wherein the central portion has a gradually sloping central depression therein and wherein a resilient o-ring which is circumjacent the central portion constitutes the immobilizing means, the o-ring having a thickness which is greater in dimension than the maximum thickness of the central portion at its periphery.

20. The stethoscope chestpiece of any of embodiments 17 to 19, wherein the ejector mark is positioned proximate to the outer rim portion.

21. The stethoscope chestpiece of any of embodiments 1 to 20, further comprising chrome plating disposed on a surface of the stethoscope chestpiece.

22. A stethoscope comprising:
the stethoscope chestpiece of any of embodiments 1 to 21;
a diaphragm releasably attached to the stethoscope chestpiece.

23. The stethoscope of embodiment 22, further comprising:
a headset comprising removable ear tips;
tubing, wherein the ear tips are fluidically coupled to the stethoscope chestpiece through the tubing.

24. A method of making a metal stethoscope comprising:
injection molding, extruding, or pressing a metallic thermoplastic composition into a mould forming a green molded body, debinding, continuously, a portion of binder material from green molded body at a temperature in a range of 100 to 200° C. over a period from 4 to 12 hours in a nitrogen-comprising atmosphere forming a brown molded body, wherein the temperature is maintained within +/−20° C. during the period;

sintering the brown molded body at a temperature in a range from 100 to 1500° C. over a period of from 6 to 10 hours in a hydrogen or argon atmosphere to form the stethoscope chestpiece.

25. The method of embodiment 24, wherein the mould comprises a negative of one or more ejectors.

26. The method of embodiment 24 or 25, wherein the mould comprises a negative forming:

a body member having a first generally bell-shaped recess with an inner central portion, an outer rim portion and a bore extending through the body member communicating with the central portion of the first recess;

immobilizing means situated on the body member and located within the first recess at about the central portion, the immobilizing means adapted to be contacted by a diaphragm when the diaphragm is in the inner position so that the stethoscope chestpiece will pass low frequency sounds and attenuate high frequency sounds when the diaphragm is in the outer position and between the outer and inner positions, and when the diaphragm is in the inner position the acoustical stiffness of the diaphragm will be sufficiently higher than the first acoustical stiffness so that the stethoscope chestpiece will pass high frequency sounds and attenuate low frequency sounds.

27. The method of embodiment 26, further comprising a second conical-shaped recess located within the first bell-shaped recess and emanating from the base of the first bell-shaped recess, the second recess being formed by the immobilizing means and the central portion of the body member.

28. The method embodiment 27, wherein the negative forms a first generally bell-shaped recess having the ejector mark disposed thereon.

29. The method of any of embodiments 24 to 25, wherein the mould comprises a negative forming a stethoscope chestpiece comprising:
a body member having a first generally bell-shaped recess with an inner central portion, an outer rim portion, and a bore extending through the body member communicating with the central portion of the first recess;
immobilizing means situated on the body member and located within the first recess at about the boundary between the outer rim portion and the inner central portion and together with the central portion forming second shallow and generally conical-shaped recess within the first recess, the immobilizing means adapted to be contacted by a diaphragm and to immobilize the diaphragm when the diaphragm is in the inner position so that the stethoscope chestpiece will pass low frequency sounds and attenuate high frequency sounds when the diaphragm is in the outer position and between the outer and inner positions, and when the diaphragm is in the inner position the acoustical stiffness of the diaphragm will be significantly higher than the first acoustical stiffness so that the stethoscope chestpiece will pass high frequency sounds and attenuate low frequency sounds.

30. The method of embodiment 29, wherein the second conical-shaped recess is formed by a plate-like member having a gradually sloping central depression therein.

31. The method of embodiment 29, wherein the mould forms the ejector marks proximate to the outer rim portion.

32. The method of any of embodiments 24 to 31, further comprising chrome plating; disposed on a surface of the stethoscope chestpiece.

33. The method of any of embodiments 24 to 31, wherein the sintering and debinding occur in the same continuous process.

34. The method of any of embodiments 24 to 31, wherein the stethoscope chestpiece has a silver color prior to polishing.

35. The method of any of embodiments 24 to 34, wherein the metallic thermoplastic composition comprises at least one polyoxymethylene homopolymer or copolymer as a binder and steel.

36. The method of any of embodiments 24 to 35, wherein the metallic thermoplastic composition comprises iron and chromium.

37. The method of any of embodiments 24 to 36, wherein the metallic thermoplastic composition is Catamold LG+.

38. The method of any of embodiments 24 to 37, wherein the mould forms a stethoscope chestpiece that is single-sided meaning that only one diaphragm can be positioned on the stethoscope chestpiece.

39. The method of any of embodiments 24 to 38, wherein the green molded body is at least 15% larger than a resulting stethoscope chestpiece.

40. The method of any of embodiments 24 to 39, wherein the green molded body is at least 10% larger than a resulting stethoscope chestpiece.

41. The method of any of embodiments 24 to 40, wherein the stethoscope chestpiece has an unpolished surface roughness (Ra) of no greater than 1.6 microns.

42. The method of any of embodiments 24 to 41, wherein the stethoscope chestpiece has a final weight of at least 50 g.

43. The method of any of embodiments 24 to 42, further comprising polishing the stethoscope chestpiece to a reflective finish.

44. The method of any of embodiments 24 to 43, further comprising depositing a thin metallic film onto one or more surfaces using physical vapor deposition.

45. The method of any of embodiments 24 to 44, further comprising: attaching a stem to a portion of the stethoscope chestpiece.

46. The method of any of embodiments 24 to 45, further comprising: attaching tubing to the stem, wherein the tubing is also connected to a yoke and eartips.

47. The method of any of embodiments 24 to 46, further comprising: attaching a diaphragm to the stethoscope chestpiece.

What is claimed is:

1. A stethoscope chestpiece comprising:
a body member having a bottom surface;
an ejector mark disposed on the bottom surface;
wherein the stethoscope chestpiece has a weight of at least 50 g, and a surface roughness ($R_a$) no greater than 1.6 microns in an unpolished state and reflectivity (% R) of at least 60% in an unpolished state,
wherein the stethoscope chestpiece has been produced by injection molding, extruding, or pressing a metallic thermoplastic composition into a mould forming a green molded body,
debinding a portion of binder material from green molded body to form a brown molded body without reducing the temperature by more than 80° C.;
sintering the brown molded body to form the stethoscope chestpiece.

2. The stethoscope chestpiece of claim 1, wherein the ejector mark is recessed and comprises a side wall and at least one major surface contacting the side wall.

3. The stethoscope chestpiece of claim 1, wherein the stethoscope chestpiece is non-symmetrical.

4. The stethoscope chestpiece of claim 1, wherein the stethoscope chestpiece has a thick portion and a thin portion.

5. The stethoscope chestpiece of claim 1, wherein the stethoscope chestpiece is further polished to a reflective finish.

6. The stethoscope chestpiece of claim 5, wherein the stethoscope chestpiece comprises a thin metallic film deposited by physical vapor deposition.

7. The stethoscope chestpiece of claim 1, wherein the metallic thermoplastic composition has a melt flow index of at least 800 g/ 10 mins as measured using ISO 1133 (190 deg. C., 21.6 kg).

8. The stethoscope chestpiece of claim 1 wherein the body member having a first generally bell-shaped recess with an inner central portion, an outer rim portion and a bore extending through the body member communicating with the central portion of the first recess;
further comprising immobilizing means situated on the body member and located within the first recess at about the central portion, the immobilizing means adapted to be contacted by a diaphragm when the diaphragm is in an inner position so that the stethoscope chestpiece will pass low frequency sounds and attenuate high frequency sounds when the diaphragm is in the outer position and between the outer and inner positions, and when the diaphragm is in the inner position an acoustical stiffness of the diaphragm will be sufficiently higher than the first acoustical stiffness so that the stethoscope chestpiece will pass high frequency sounds and attenuate low frequency sounds.

9. The stethoscope chestpiece of claim 8, further comprising a second conical-shaped recess located within the first bell-shaped recess and emanating from a base of the first bell-shaped recess, the second recess being formed by the immobilizing means and the central portion of the body member.

10. The stethoscope chestpiece of claim 8, wherein the ejector mark is disposed within the first generally bell-shaped recess.

11. A stethoscope comprising:
the stethoscope chestpiece of claim 1;
a diaphragm releasably attached to the stethoscope chestpiece.

12. The stethoscope of claim 11, further comprising:
a headset comprising removable ear tips;
tubing, wherein the ear tips are fluidically coupled to the stethoscope chestpiece through the tubing.

13. A method of making a metal stethoscope comprising:
injection molding, extruding, or pressing a metallic thermoplastic composition into a mould forming a green molded body,
continuously debinding a portion of binder material from green molded body at a temperature in a range of 100 to 200° C. over a period from 4 to 12 hours in a nitrogen-comprising atmosphere forming a brown molded body, wherein the temperature is maintained within ±10° C. during the period;
sintering the brown molded body at a temperature in a range from 1100 to 1500° C. over a period of from 6 to 10 hours in a hydrogen or argon atmosphere to form the stethoscope chestpiece.

14. The method of claim 13, further comprising: removing the green molded body from the mould by applying ejector pins and forming an ejector mark in the green molded body.

15. The method of claim 13, wherein the mould comprises a negative forming:
a body member having a first generally bell-shaped recess with an inner central portion, an outer rim portion and a bore extending through the body member communicating with the central portion of the first recess;
immobilizing means situated on the body member and located within the first ecess at about the central portion, the immobilizing means adapted to be contacted by a diaphragm when the diaphragm is in an inner position so that a stethoscope chestpiece will pass low frequency sounds and attenuate high frequency sounds when the diaphragm is in the outer position and between the outer and inner positions, and when the diaphragm is in the inner position the acoustical stiffness of the diaphragm will be sufficiently higher than the first acoustical stiffness so that the stethoscope chestpiece will pass high frequency sounds and attenuate low frequency sounds.

16. The method of claim 15, wherein the ejector mark is formed proximate to the immobilizing means.

17. The method of claim 13, wherein the metallic thermoplastic composition is Catamold LG+.

18. The method of claim 13, wherein the sintering and debinding occur in the same continuous process.

19. The method of claim 13, further comprising polishing a stethoscope chestpiece to a reflective finish.

20. The method of claim 19, further comprising depositing a thin metallic film onto one or more surfaces using physical vapor deposition.

* * * * *